United States Patent [19]
Bell et al.

[11] Patent Number: 5,280,741
[45] Date of Patent: Jan. 25, 1994

[54] THREAD DISPENSER WITH CUTTER

[75] Inventors: Joseph V. Bell, Santa Barbara; Eric Groth, Camarillo, both of Calif.

[73] Assignee: Belport Company, Inc., Camarillo, Calif.

[21] Appl. No.: 5,847

[22] Filed: Jan. 19, 1993

[51] Int. Cl.$^5$ .................. B65D 51/24; B65D 85/04
[52] U.S. Cl. .......................... 83/175; 83/375; 83/649; 225/6
[58] Field of Search ............ 83/175, 649, 375; 225/6

[56] References Cited

U.S. PATENT DOCUMENTS

| | | | |
|---|---|---|---|
| 294,312 | 2/1884 | Earl | 225/6 |
| 1,858,134 | 5/1932 | Booth et al. | 225/6 |
| 5,107,732 | 4/1992 | Hanmer | 83/175 |
| 5,133,980 | 7/1992 | Ream et al. | 83/649 |
| 5,146,828 | 9/1992 | Huang et al. | 83/649 |

Primary Examiner—Hien H. Phan
Attorney, Agent, or Firm—Jack C. Munro

[57] ABSTRACT

A dispenser for a quantity of a retraction cord where the cord is impregnated with a medicinal substance. The outer free end of the cord is conducted through an outlet hole formed within a cover which closes the access opening into the internal chamber of the housing where the cord stored. A lid is mounted on the cover with this lid including a cutting blade. This lid is movable between an open and a closed position and when in the open position the free outer end of the cord can be pulled from the dispenser a desired amount. As the lid is closed, the cutting blade severs the cord permitting the severed strand of the cord to be utilized. The remaining cord within the dispenser is closed to the ambient thereby keeping the stored cord in the dispenser from contamination.

4 Claims, 1 Drawing Sheet

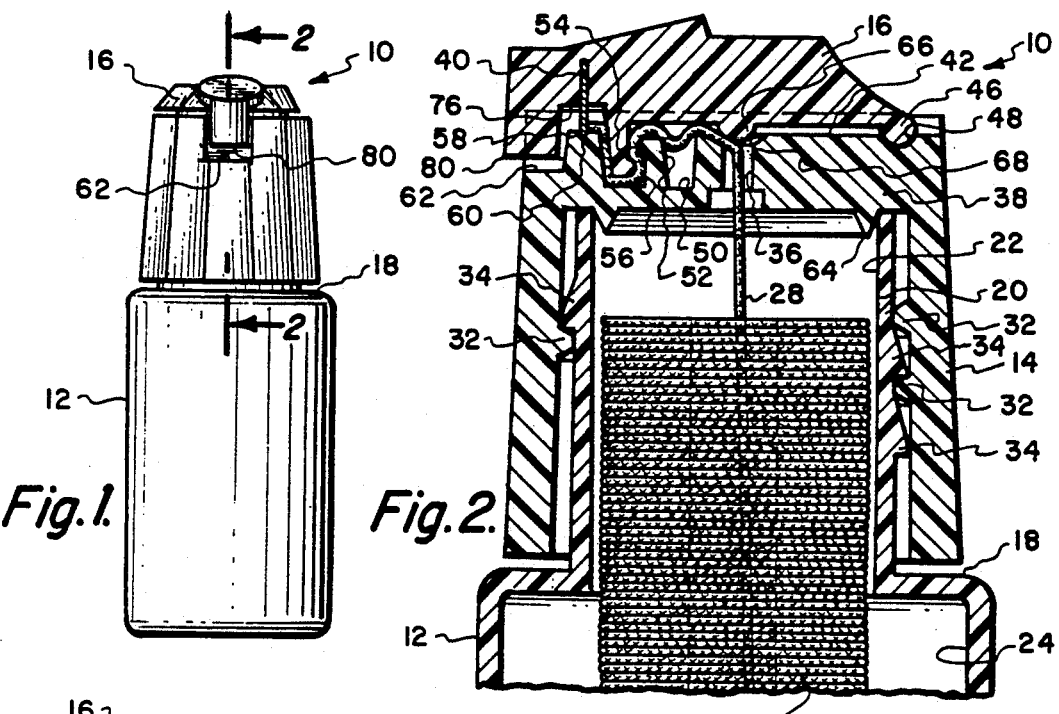
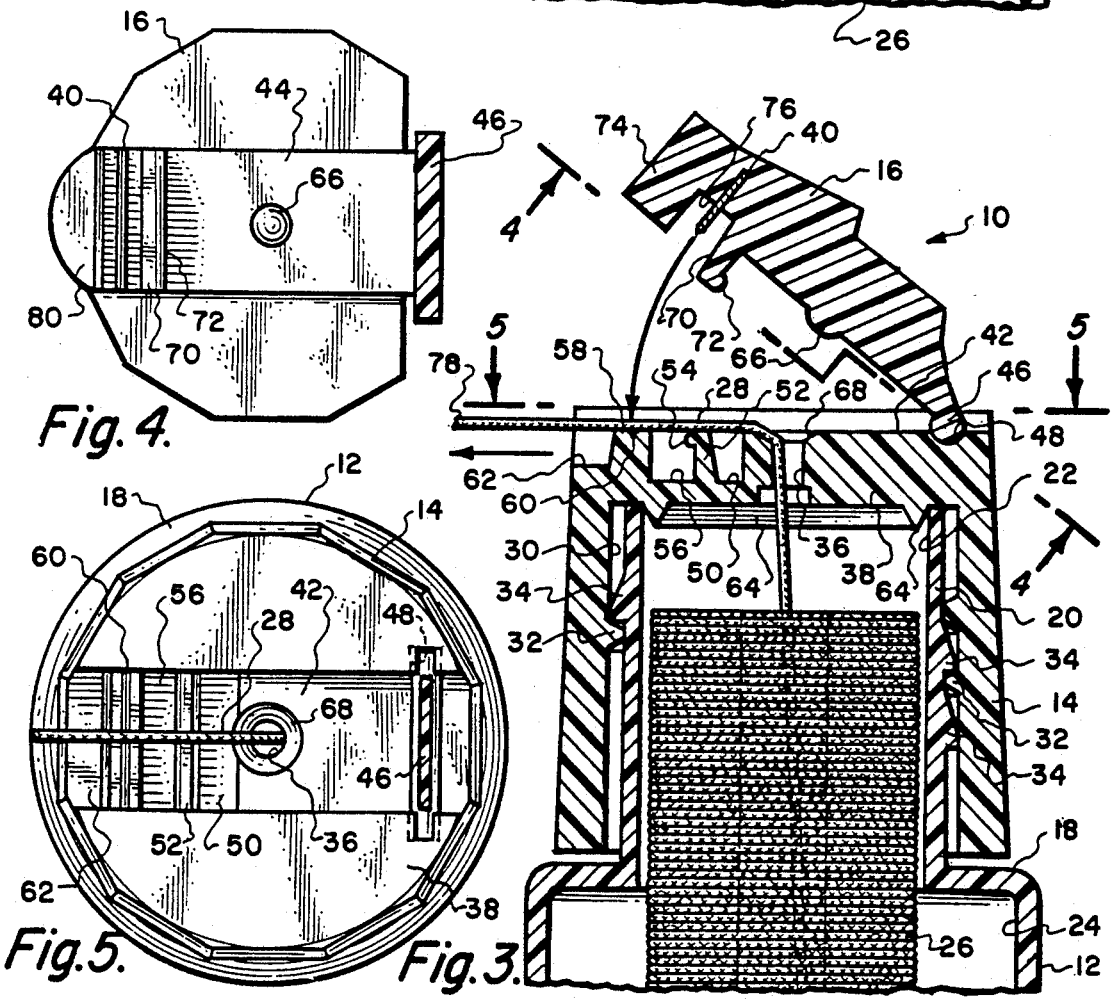

THREAD DISPENSER WITH CUTTER

BACKGROUND OF THE INVENTION

1. Field of the Invention

The field of this invention relates to dispensers and more particularly to a dispenser for a coiled quantity of thread known in the dental field as retraction cord particularly where the cord includes a dehydrated dental solution.

2. Description of Prior Art

Dispensers for thread have long been known. A typical dispenser for a thread is exposed to ambient air. However, where the thread is impregnated with a solution, it is desirable to construct a dispenser so as to prevent contamination of the cord. A typical usage of a liquid impregnated cord would be in the dental field. Cords are impregnated with an astringent, antiseptic, antibiotic, hemostyptic or other type of solution. The dentist is to utilize this cord in conjunction with the teeth of the human being at a particular selected location within the mouth to achieve a certain desired end result. A typical end result would be for retraction of the gum away from a tooth so as to facilitate preparation of a particular tooth for an impression to create a prosthetic.

The typical procedure for the dentist is to open the container in order to gain access to free the outer end of the quantity of cord that is contained within. The dentist or dental technician then stretches out a desired length of the cord and severs it with a cutting tool such as scissors. The container is then closed to prevent contamination of the cord until such time that another length of the cord is desired; at which time the procedure is repeated.

In the past it has been common to design a container where the cord protrudes through a small outlet opening of the container. The container includes a lid. In the past, it has been common, when the lid is moved to the open position, to permit extraction of the cord, the cord will fall, by gravity, back into the inside of the container. This requires the container to be completely opened and a section of cord to be reinserted through the outlet opening in the cover of the container prior to a section of thread being selected and removed by the scissors. When the free outer end of the cord falls within the interior container, such extraction of the cord then becomes a time consuming and contaminating procedure. As is well known, the time of a dentist is exceedingly valuable and therefore the time lost in repeatedly obtaining of such a section of cord (over a period of time such as a year) is rather costly.

In most instances when it is desired that a given length of retraction cord is needed, the dentist is in the middle of some procedure within the patient's mouth. Typical prior art severing of such a cord is a two-handed procedure which requires the use of a separate tool such as scissors. It would be desirable to construct a dispenser which facilitates the dispensing procedure primarily by eliminating the use of a separate cutting tool.

SUMMARY OF THE INVENTION

The structure of the present invention relates to a dispenser for cord where the dispenser includes a housing which has an internal compartment. Within this internal compartment is located a quantity of a cord generally in a coil. Normally, this cord will be impregnated with a liquid medicinal preparation and then dehydrated. It is important that the product not become contaminated so that a known precise clean quantity of the retraction cord will be applied with each and every given length of the cord. The outer free end of the cord is conducted through an outlet opening formed within a cover. The cover closes the access opening into the internal chamber. Within the cover there is formed a cutting ledge. The cutting ledge is located between two recesses. A lid is pivotally mounted on the cover and is movable from an open position, permitting removal of the cord, to a closed position which closes the cord in the internal chamber to the ambient. There are a pair of protuberances on the lid each of which respectively engages with a recess formed in the cover and causes stretching of the cord across the cutting ledge when the lid is closed. When the lid is fully moved to the closed position there is mounted within the lid a cutting blade which presses against the cutting ledge thereby severing the cord stretched there across. The severed section of cord can now be disengaged from the dispenser and used by the dentist or dental technician. The next time the lid is opened and a new section of cord is desired, the outermost portion of the cord is still pressed into one of the recesses formed within the cover so as to prevent the cord from falling back into the internal chamber providing access to grasp the cord and extract another desired length.

The primary objective of the present invention is to incorporate a cutting device in conjunction with a cord dispenser thereby eliminating the need for the use of a separate cutting tool such as scissors.

Another objective of the present invention is to construct a cord dispenser with a cutting blade where the cord dispenser can be manufactured inexpensively thereby minimizing the cost of the cord and dispenser to the user.

Another objective of the present invention is to construct a dispenser for cord which substantially insures that the cord is also readily available to be grasped each and every time a desired length of cord is to be obtained.

BRIEF DESCRIPTION OF THE DRAWING

FIG. 1 is a front elevational view of the dispenser of the present invention showing the lid of the dispenser in the closed position;

FIG. 2 is a cross-sectional view taken along line 2—2 of FIG. 1 showing the lid again in the closed position;

FIG. 3 is a cross-sectional view similar to FIG. 2 but showing the lid in the open position and a section of the cord being stretched from the internal chamber of the dispenser;

FIG. 4 is a bottom view of the lid incorporated within the dispenser of the present invention taken along line 4—4 of FIG. 3 with the hinge between the lid and the cover being shown in cross section; and FIG. 5 is a top view of the cover utilized in conjunction with the dispenser of the present invention taken along line 5—5 of FIG. 3 again showing the hinge joint in cross section.

DETAILED DESCRIPTION OF THE SHOWN EMBODIMENT

Referring particularly to the drawing there is shown the dispenser 10 of this invention which includes generally a housing 12, a cover 14 and a lid 16. The housing 12 is basically cylindrical and has a closed bottom from which extends upwardly an integral sidewall which includes an inwardly extending annular flange 18. Extending upwardly from the annular flange 18 is a tubular section 20 which has an open upper end defining an access opening 22. The access opening 22 permits access into an internal chamber 24 formed within the housing 12. To be contained within the internal chamber 24 is a quantity of a cord in the form of a coil 26. This coil 26 has an outer free end defined as a strand 28.

The coil 26 is to be located within the internal chamber 24 during the time that the cover 14 is disengaged from the tubular section 20. The cover 14 includes an enlarged internal recess 30 the wall of which includes a series of screw threads 32. Tubular section 20 has formed on its exterior surface a spiral screw thread 34. Prior to installation of the cover 14 onto the tubular section 20, the strand 28 of the coil 26 is conducted through the outlet hole 36 which is centrally formed within the top end 38 of the cover 14. Once the strand 28 is conducted through the outlet hole 36, the cover 14 is then placed on the tubular section 20 and then twisted relative thereto until the cover 14 is tightly installed in position on the tubular section 20. This position is clearly shown in FIGS. 2 and 3 of the drawing.

It is to be understood that the entire dispenser 10 of this invention will be constructed of plastic with the possible exception of the cutting blade 40.

The top 38 includes a strip section 42. The underside of the lid 16 also includes a strip section 44. The width of the strip sections 42 and 44 are essentially identical. The lid 16 has a back edge which is formed into an elongated rod like member 46. This member 46 fits within elongated groove 48 formed within the top 38. The connection between the member 46 and the groove 48 forms a hinge joint permitting pivoting of the lid 16 between an open position shown in FIG. 3 to a closed position shown in FIG. 2.

Formed within the strip section 42 and directly adjacent the outlet hole 36 is a recess 50. The outer wall of the recess 50 is formed into a deflectable wall 52 with this wall 52 having an exterior surface which includes a horizontal locking rib 54. This horizontal locking rib 54 is mounted on the inner wall of recess 56 which is also located in the strip section 42. The outer wall of the recess 56 is formed by means of a cutting ledge 58. Formed within the upper surface of the cutting ledge 58 is an elongated groove 60. The cutting ledge 58 is also formed within the strip 42. The outer wall of the cutting ledge 58 forms the inner wall of recess 62.

Underneath the top 38 there is formed an annular ridge 64. This ridge 64 functions to form a tight seal with the tubular section 20 at the access opening 22 when the cover 14 is tightly installed in conjunction with the tubular section 20. The under surface of the lid 16 includes a centrally located rounded protrusion 66. When the lid 16 is in the closed position, the centrally located rounded protrusion 66 is to engage with chamfered area 68 of the outlet hole 36. The rounded protrusion 16 is formed within the strip section 44.

Also formed within the strip section 44 and spaced from the rounded protrusion 66 is an elongated lineal protrusion 70. The inside surface of the wall of the protrusion 70 includes a lineal protuberance 72. When the lid 16 is in the closed position, the protuberance 72 is to slide over protuberance 54 at which time the wall 54 will slightly deflect rearwardly which is accommodated for by the inclusion of the recess 50. As the protrusion 72 passes over protrusion 54, the wall 52 will deflect in an outward direction. When protrusion 72 passes beyond protrusion 54, walls 52 will deflect back to its normal at rest position with there occurring a locking action between the lid 16 and the top 38 of the cover 14.

Within the recess 56 a section of the outer free end 28 of the thread is bound between the protuberance 70 and the recess 56. When the lid 16 is closed, there is an outer ridge 74 of the lid 16 which engages with the recess 62 again clamping the strand 28 of the thread therebetween. This causes the cord to be stretched tightly across the cutting ledge 58. Just as the lid 16 reaches a fully closed position, the lineal cutting blade 40, which is fixedly mounted within the lid 16 and connects with recess 76 formed within the under surface of the lid 16, will sever the stretched section of the strand 28 located across cutting ledge 58. The sharp point of the cutting blade 40 is to engage with the groove 60. The net result is there is a removed strand 78 of the cord which then can be utilized by the user at any desired location.

Simultaneously with the closing of the lid 16, not only is the strand 28 severed but the remaining portion of the cord is closed to the ambient to prevent contamination of the medicament impregnated within the strand or evaporation of a liquid medicament 28 and the coil 26. When it is desired to again obtain a further strand 78 to be removed, the user presses upwardly against flange 80 of the lid 16 which will permit the lid 16 to be moved from the closed position to the open position shown in FIG. 3. During this movement, strand 28 should still be caused to remain within the recess 56 which will prevent the strand 28 from falling by gravity through the outlet hole 36 into the internal chamber 24. This should locate the strand 28 so as to be readily graspable by the user so that again the thread 28 can be stretched in an outward direction and the lid 16 again closed and a new strand 78 now being obtained to be used.

What is claimed is:

1. A dispenser comprising:

a housing having an internal compartment, said internal compartment having an access opening permitting access to said internal compartment, said internal compartment adapted to contain a quantity of a liquid impregnated cord with this cord having an outer free end;

a cover mounted on said housing closing said access opening, said cover including an outlet hole, said outlet hole adapted to permit exit of the outer free end of the cord, said cover having a cutting ledge located spaced from said outlet hole;

a lid mounted on said cover, said lid being movable on said cover between an open position and a closed position, said closed position closing said outlet hole to the ambient, said open position exposing said outlet hole to the ambient;

said cover including a first clamping recess, a first protuberance mounted on said lid, said first protuberance to engage with said first clamping recess when said lid is in said closed position thereby binding the cord therebetween, said first clamping recess to retain said outer free end of said cord after severing and upon movement of said lid to said open position to prevent retraction of said cord through said outlet hole into said internal compartment so as to provide for manual accessibility to said outer free end to permit moving of said outer free end to an extended position;

a second clamping recess formed within said cover, a second protuberance mounted within said lid, said second protuberance to matingly engage said second clamping recess as said lid is moved from said open position to said closed position, said cutting ledge being located between said first clamping recess and said second clamping recess thereby causing the cord to be stretched across said cutting ledge as said lid assumes said closed position; and a cutting blade mounted in said lid between said first and second protuberances, said cutting blade engages said cutting ledge when said lid is in said closed position and as the cord is stretched taut across said cutting ledge, severs the cord as said lid is moved from said open position to said closed position.

2. The dispenser as defined in claim 1 wherein:
said cutting ledge including a groove, said cutting blade to extend within said groove when said lid is in said closed position.

3. The dispenser as defined in claim 1 wherein:
locking means connected between said lid and said cover, said locking means being engaged when said lid is in said closed position.

4. The dispenser as defined in claim 3 wherein:
said locking means being associated with said first clamping recess and said first protuberance, thereby as said first protuberance connects with said first clamping recess said locking means is automatically engaged.

* * * * *